United States Patent
Miyaguchi (10) Patent No.: US 7,091,465 B2
(45) Date of Patent: Aug. 15, 2006

(54) IMAGE SENSOR WITH A VOLTAGE MAINTAINING CAPACITOR AND AN AC-SIGNAL BLOCKING RESISTOR, AND IMAGING SYSTEM COMPRISING THE IMAGE SENSOR

(75) Inventor: Kazuhisa Miyaguchi, Hamamatsu (JP)

(73) Assignee: Hamamatsu Photonics K.K., Shizuoka (JP)

( * ) Notice: Subject to any disclaimer, the term of this patent is extended or adjusted under 35 U.S.C. 154(b) by 91 days.

(21) Appl. No.: 10/466,336

(22) PCT Filed: Oct. 30, 2002

(86) PCT No.: PCT/JP02/11301

§ 371 (c)(1),
(2), (4) Date: Jul. 21, 2004

(87) PCT Pub. No.: WO03/043317

PCT Pub. Date: May 22, 2003

(65) Prior Publication Data

US 2004/0238721 A1   Dec. 2, 2004

(30) Foreign Application Priority Data

Nov. 15, 2001 (JP) ............................. 2001-350603

(51) Int. Cl.
  *H01L 27/00* (2006.01)
(52) U.S. Cl. ................ 250/208.1; 250/370.09

(58) Field of Classification Search ............. 250/208.1, 250/214 R, 370.09
See application file for complete search history.

(56) References Cited

U.S. PATENT DOCUMENTS 6,201,249 B1    3/2001  Yamayoshi ............ 250/370.11
2001/0025913 A1*  10/2001  Tanimoto ................. 250/208.1

FOREIGN PATENT DOCUMENTS

| EP | 904734 A | 3/1999 |
| JP | 7-236093 A | 9/1995 |
| JP | HEI 11-104128 | 4/1999 |
| JP | 2000-254115 | 9/2000 |
| JP | 2000-254115 A | 9/2000 |
| JP | 2001-252266 A | 9/2001 |

\* cited by examiner

*Primary Examiner*—Thanh X. Luu
(74) *Attorney, Agent, or Firm*—Drinker, Biddle & Reath LLP (57) ABSTRACT

An image sensor 100 is provided with a first voltage maintainer 61 including two first voltage maintaining capacitors $C_{1Va}$, $C_{1Vb}$ for maintaining a voltage of signal input electrode 47, and a second voltage maintainer 62 including a second voltage maintaining capacitor $C_{2V}$ for maintaining a voltage of bias voltage input electrode 46. This image sensor 100, even in a disconnected state from main body part 200, is able to maintain the voltage of bias voltage input electrode 46 and the voltage of signal input electrode 47 during an image pickup operation and thus to implement image pickup.

7 Claims, 7 Drawing Sheets

IMAGE SENSOR WITH A VOLTAGE MAINTAINING CAPACITOR AND AN AC-SIGNAL BLOCKING RESISTOR, AND IMAGING SYSTEM COMPRISING THE IMAGE SENSOR

TECHNICAL FIELD

The present invention relates to an image sensor including an array of pixels to generate their respective charges in response to incidence of light, and an imaging system using the image sensor.

BACKGROUND ART

An image sensor includes an array of pixels to generate their respective charges in response to incidence of light and is configured to output electric signals according to amounts of the charges generated in the respective pixels.

An intraoral sensor is one of such image sensors. This intraoral sensor is configured to transmit the electric signals according to amounts of charges through a cable (about two to three meters) to the main body part. The main body part connected to the intraoral sensor operates to display an image generated on the basis of the transmitted electric signals, on a display device or print the image by a printer. The cable connecting the intraoral sensor to the main body part is also used to feed clock signals to order transfer of the charges generated in the respective pixels, and to output bias voltages to the intraoral sensor.

The presence of the cable connecting the intraoral sensor to the main body part can cause such an accident that the cable is accidentally caught on something during use of the intraoral sensor, so as to result in breaking the intraoral sensor. This is also the case with the image sensors connected through the cable to the main body part, as well as the intraoral sensors.

There were thus proposals on techniques of eliminating the need for the cable connecting the image sensor to the main body part. For example, Japanese Patent Applications Laid-Open No. 11-104128 and No. 2001-252266 disclose the image sensor incorporating a battery and others and configured to perform radio communication with the main body part, and the imaging system using the image sensor. The techniques disclosed in these Applications obviate the need for the cable connecting the image sensor to the main body part.

DISCLOSURE OF THE INVENTION

However, while the techniques disclosed in these Applications can obviate the need for the cable connecting the image sensor to the main body part, they are disadvantageous in terms of cost, size, and weight because of the inclusion of the battery and radio system in the image sensor, and also involve a problem that the configuration of the image sensor itself becomes complicated.

The present invention has been accomplished in order to solve the above problem and an object of the present invention is to provide an image sensor constructed in an inexpensive and simple configuration without need for use of the cable connecting the image sensor to the main body part, and an imaging system using the image sensor.

An image sensor according to the present invention is an image sensor having an image pickup part including an array of pixels to generate their respective charges in response to incidence of light, a readout part for outputting electric signals according to the charges generated in the respective pixels, a signal input electrode for inputting a clock signal to order transfer of the charge, into each of the pixels, and a bias voltage input electrode for inputting a bias voltage supplied to the image pickup part and to the readout part, the image sensor comprising: first voltage maintaining means connected to the signal input electrode and comprising a first voltage maintaining capacitor for maintaining a voltage of the signal input electrode; and second voltage maintaining means connected to the bias voltage input electrode and comprising a second voltage maintaining capacitor for maintaining a voltage of the bias voltage input electrode.

Another image sensor according to the present invention comprises an image pickup part comprising an array of pixels each comprised of a photoelectric conversion part to generate a charge in response to incidence of light and a signal input electrode for inputting a clock signal to order transfer of the charge; a readout part for outputting electric signals according to the charges generated in the respective pixels; a bias voltage input electrode for inputting a bias voltage supplied to the photoelectric conversion part and to the readout part; a clock signal input terminal for receiving supply of the clock signal from the main body part when the image sensor is connected to the main body part; first voltage maintaining means connected to the signal input electrode in parallel with the clock signal input terminal and comprising a first voltage maintaining capacitor for maintaining a voltage of the signal input electrode; a bias voltage input terminal for receiving supply of the bias voltage from the main body part when the image sensor is connected to the main body part; and second voltage maintaining means connected to the bias voltage input electrode in parallel with the bias voltage input terminal and comprising a second voltage maintaining capacitor for maintaining a voltage of the bias voltage input electrode.

This permits the image sensor to maintain the voltage of the signal input electrode by the first voltage maintaining capacitor in the first voltage maintaining means and to maintain the voltage of the bias voltage input electrode by the second voltage maintaining capacitor in the second voltage maintaining means. When light is incident into the image pickup part in this state, each of the pixels generates a charge in response to the incidence of the light and the charge thus generated is stored in the pixel having generated the charge.

Accordingly, the image sensor alone can perform the image pickup operation, without need for the battery and the radio system, so that the image sensor can be obtained in the inexpensive and simple configuration without need for the cable for connection to the main body part.

BEST MODE FOR CARRYING OUT THE INVENTION

Embodiments of the present invention will be described below in detail with reference to the accompanying drawings. The same elements will be denoted by the same reference symbols throughout the description of the drawings, without redundant description thereof.

Figure 1:
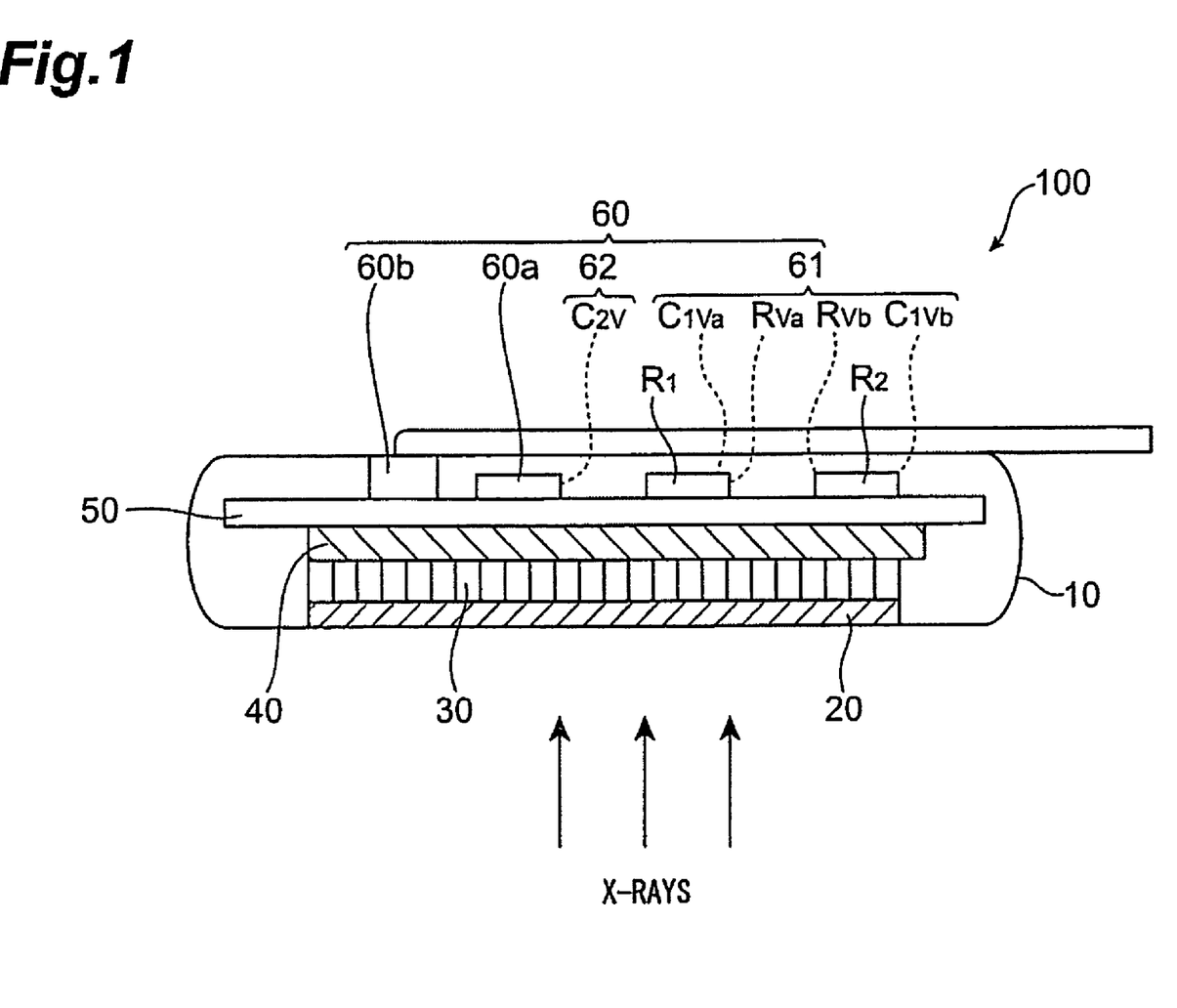
FIG. 1 is a sectional view to illustrate a configuration of image sensor 100 according to an embodiment of the invention.

First, an embodiment of the image sensor according to the present invention will be described. FIG. 1 is a sectional view to illustrate the configuration of image sensor 100 according to the present embodiment. The image sensor 100 has casing 10, scintillator 20, fiber optical plate (FOP) 30, CCD image pickup device 40, ceramic substrate 50, and external component group 60. The casing 10 covers the scintillator 20, FOP 30, CCD image pickup device 40, ceramic substrate 50, and external component group 60.

The scintillator 20 converts X-rays incident through the casing 10, into visible light. The FOP 30 guides the visible light as converted by the scintillator 20, to the CCD image pickup device 40. The CCD image pickup device 40 is provided with image pickup part 41 having a plurality of pixels $43_{1,1}$–$43_{M,N}$ to generate their respective charges in response to the visible light guided thereinto by the FOP 30. The pixels $43_{1,1}$–$43_{M,N}$ and the image pickup part 41 will be described later.

The external component group 60 is comprised of an integrated circuit, resistors, transistors, diodes, capacitors, connectors, etc. and is mounted on the ceramic substrate 50. These are disposed on the opposite side to the X-ray incidence side of the CCD image pickup device 40. The details of the external components 60 are illustrated in FIG. 2.

Figure 2:
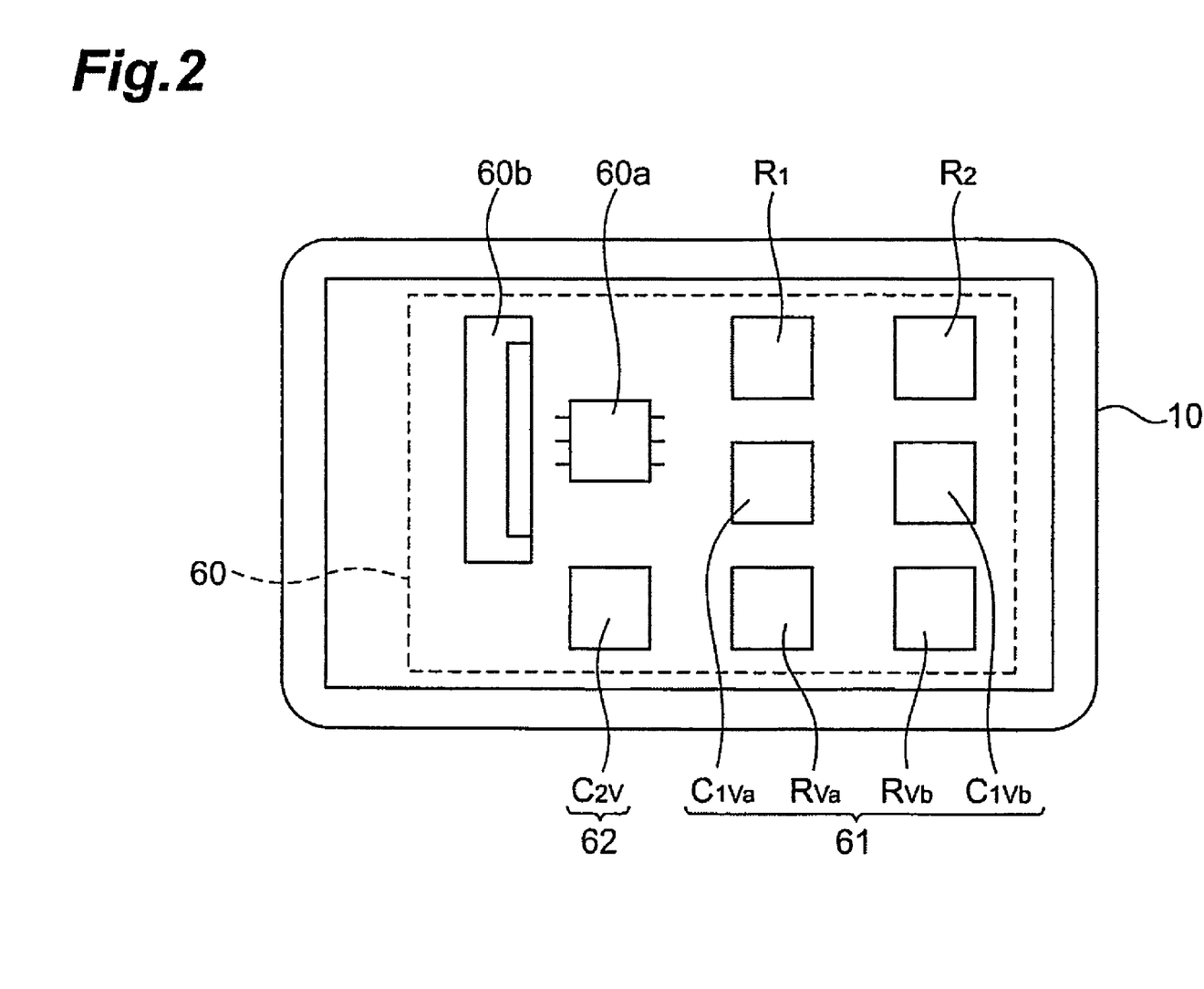
FIG. 2 is an illustration showing a configuration of external component group 60 in the image sensor 100 according to the embodiment.

FIG. 2 is an illustration showing the configuration of the external component group 60 in the image sensor 100 according to the present embodiment. As shown in FIG. 2, the external component group 60 includes integrated circuit 60a, connector 60b, first clock signal input resistor $R_1$, second clock signal input resistor $R_2$, first voltage maintainer (first voltage maintaining means) 61, and second voltage maintainer (second voltage maintaining means) 62. The first voltage maintainer 61 includes two first voltage maintaining capacitors $C_{1Va}$, $C_{1Vb}$ and two ac-signal blocking resistors $R_{Va}$, $R_{Vb}$, and the second voltage maintainer 62 includes a second voltage maintaining capacitor $C_{2V}$. The external component group 60 also includes transistors and diodes (not shown) in addition to the above components.

The integrated circuit 60a is configured to perform input/output of various signals and others. The connector 60b is connected to an outgoing line such as a flexible cable, and is configured to be connected through the outgoing line to main body part 200 described hereinafter. The other components will be detailed later with FIG. 5, and the main body part 200 with FIG. 6.

Figure 3:
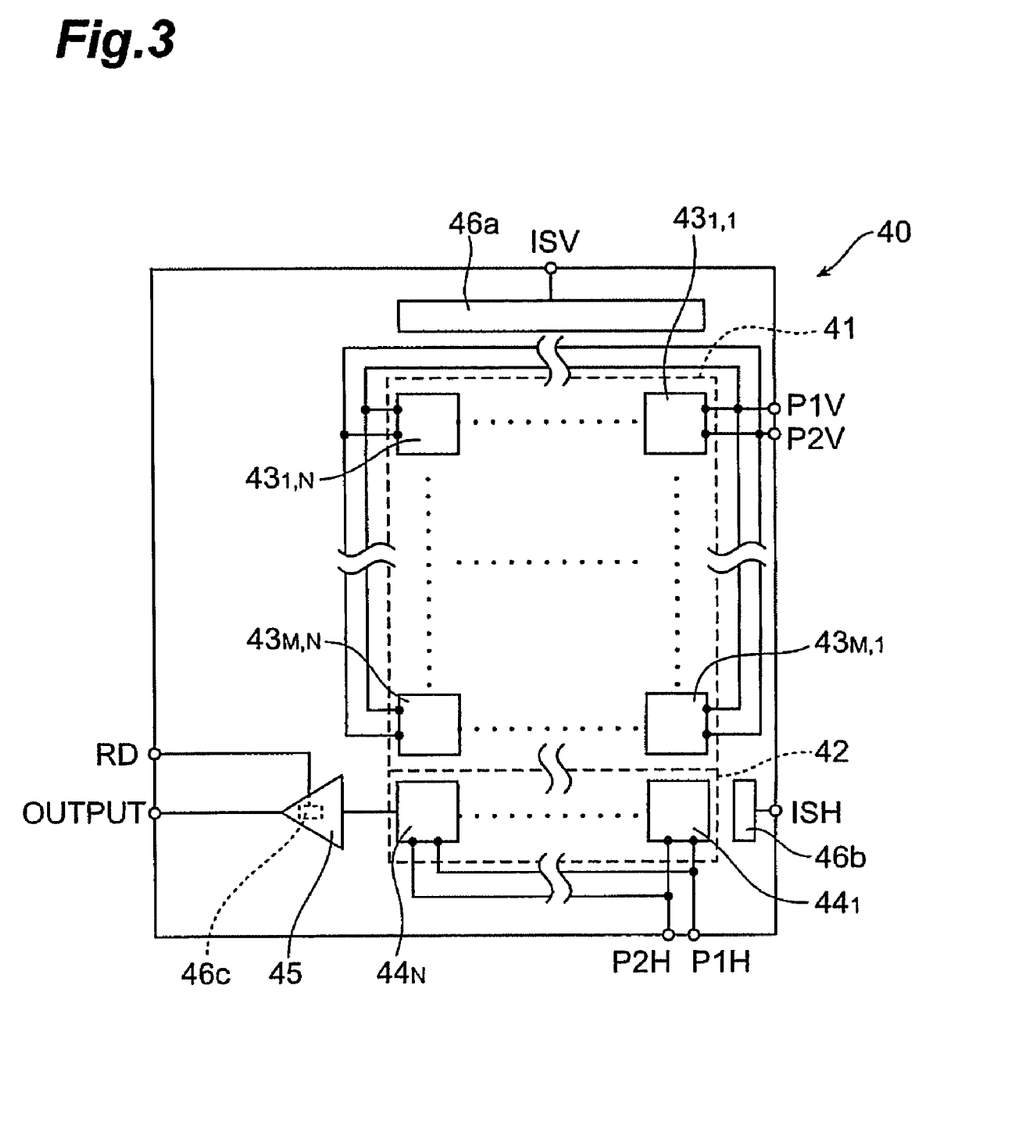
FIG. 3 is a top plan view to illustrate a configuration of CCD image pickup device 40 in the image sensor 100 according to the embodiment.
Figure 4:
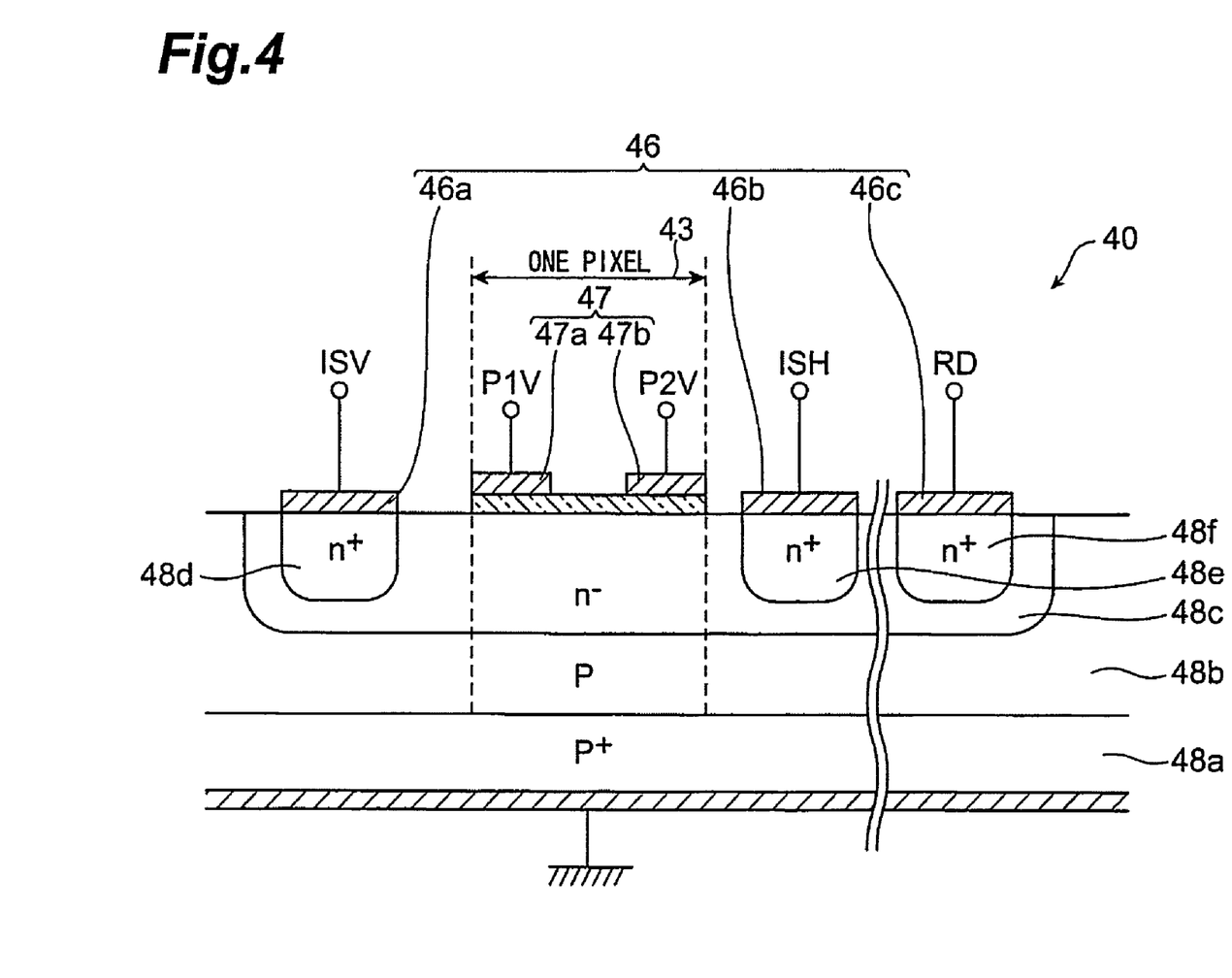
FIG. 4 is a sectional view to illustrate the configuration of CCD image pickup device 40 in the image sensor 100 according to the embodiment.

The configuration of CCD image pickup device 40 will be described below with reference to FIGS. 3 and 4. FIG. 3 is a top plan view to illustrate the configuration of CCD image pickup device 40 in the image sensor 100 according to the present embodiment, and FIG. 4 a sectional view to illustrate the configuration of CCD image pickup device 40 in the image sensor 100 according to the present embodiment. The CCD image pickup device 40 includes image pickup part 41, charge output part 42, readout part 45, bias voltage input electrodes 46, and signal input electrodes 47. The image pickup part 41, charge output part 42, and readout part 45 will be described mainly with FIG. 3, and the bias voltage input electrodes 46 and signal input electrodes 47 mainly with FIG. 4.

First, the description will be given with reference to FIG. 3. The image pickup part 41 includes an array of M rows and N columns of pixels $43_{1,1}$–$43_{M,N}$, and each of the pixels $43_{1,1}$–$43_{M,N}$ generates a charge in response to incidence of the visible light as converted by the scintillator 20 and stores the charge. Clock signals P1V, P2V to order transfer of the charge are supplied into each of the pixels $43_{1,1}$–$43_{M,N}$.

The charges generated in the respective pixels $43_{1,1}$–$43_{M,N}$ are outputted from the image pickup part 41 to the charge output part 42, based on switching of logical levels of the clock signals P1V, P2V between a high level and a low level.

The charge output part 42 takes in the charges outputted from the image pickup part 41. This charge output part 42 has a plurality of areas $44_1$–$44_N$, and other clock signals P1H, P2H to order transfer of charges are supplied through other signal input electrodes to each of the areas $44_1$–$44_N$.

The charges put into the charge output part 42 are outputted from the charge output part 42 to the readout part 45, based on switching of logical levels of the clock signals P1H, P2H between a high level and a low level.

The charges outputted from the charge output part 42 are fed into the readout part 45. The readout part 45 outputs each of electric signals according to amounts of the charges outputted from the areas $44_1$–$44_N$. Namely, the readout part 45 outputs electric signals according to the charges generated in the respective pixels $43_{1,1}$–$43_{M,N}$.

First bias voltage input electrode 46a is electrically connected to the image pickup part 41, and bias voltage ISV fed to the first bias voltage input electrode 46a is supplied to the image pickup part 41. Second bias voltage input electrode 46b is electrically connected to the charge output part 42, and bias voltage ISH fed to the second bias voltage input electrode 46b is supplied to the charge output part 42. Third bias voltage input electrode 46c is electrically connected to the readout part 45, and bias voltage RD fed to the third bias voltage input electrode 46c is supplied to the readout part 45.

Next, the description will be given with reference to FIG. 4. The CCD image pickup device 40 shown in FIG. 3 has the plurality of pixels $43_{1,1}$–$43_{M,N}$ arranged in the array of M rows and N columns in the image pickup part 41, but the pixels $43_{1,1}$–$43_{M,N}$ will be represented by one pixel 43 in FIG. 4, for simplifying the description. It is also noted that FIG. 4 is illustrated without illustration of part of the configuration, for simplification of the description, and the description will focus on the bias voltage input electrodes 46 and the region under the bias voltage input electrodes 46 and on the signal input electrodes 47 and the region under the signal input electrodes 47.

The CCD image pickup device 40 consists of $p^+$ type semiconductor substrate 48a, p-layer 48b, $n^-$ layer 48c, first $n^+$ layer 48d, second $n^+$ layer 48e, and third $n^+$ layer 48f. The $p^+$ type semiconductor substrate 48a is grounded, and the p-layer 48b is formed on the front surface side (light incidence side) of the $p^+$ layer 48a. The $n^-$ layer 48c is formed on the front surface side of the p-layer 48b. The first $n^+$ layer 48d, second $n^+$ layer 48e, and third $n^+$ layer 48f are formed so as to be surrounded by the n⁻ layer 48c. The first bias voltage input electrode 46a is connected to the front surface side of the first n⁺ layer 48d, the second bias voltage input electrode 46b to the front surface side of the second n⁺ layer 48e, and the third bias voltage input electrode 46c to the front surface side of the third n⁺ layer 48f.

The first bias voltage input electrode 46a connected to the front surface side of the first n⁺ layer 48d is provided for inputting the bias voltage ISV to be supplied to the image pickup part 41. The bias voltage ISV having a predetermined voltage value is supplied to this first bias voltage input electrode 46a during transfer of charge, and the bias voltage ISV having a voltage value lower than the predetermined voltage value of the bias voltage ISV supplied during transfer of charge is supplied to the first bias voltage input electrode 46a during the image pickup operation (the voltage value of the bias voltage ISV during the image pickup operation will be referred to hereinafter as an image pickup voltage value).

The bias voltage ISH having a predetermined voltage value to be supplied to the charge output part 42 is supplied to the second bias voltage input electrode 46b connected to the front surface side of the second n⁺ layer 48e. The bias voltage ISH having a predetermined voltage value is supplied to the second bias voltage input electrode 46b during transfer of charge, and the bias voltage ISH having a voltage value lower than the predetermined voltage value of the bias voltage ISH during transfer of charge is supplied to the second bias voltage input electrode 46b during the image pickup operation (the voltage value of the bias voltage ISH during the image pickup operation will be referred to hereinafter as an image pickup voltage value).

The bias voltage RD having a predetermined voltage value to be supplied to the readout part 45 is supplied to the third bias voltage input electrode 46c connected to the front surface side of the third n⁺ layer 48f. The bias voltage RD having a predetermined voltage value is supplied to the third bias voltage input electrode 46c during transfer of charge, and the bias voltage RD having a voltage value lower than the predetermined voltage value of the bias voltage RD during transfer of charge is supplied to the third bias voltage input electrode 46c during the image pickup operation (the voltage value of the bias voltage RD during the image pickup operation will be referred to hereinafter as an image pickup voltage value).

The above description concerned the example wherein the bias voltages during the image pickup operation were set lower than those during the transfer of charge, but the image sensor can also be configured so as to supply the same voltage value according to the voltage supplied to each of the first bias voltage input electrode 46a, the second bias voltage input electrode 46b, and the third bias voltage input electrode 46c during the image pickup operation and during the transfer of charge.

First signal input electrode 47a for inputting clock signal P1V to order transfer of charge, into pixel 43 is provided through an insulating film on the front surface side of the n⁻ layer 48c. This clock signal P1V switches its logical level in transfer of charge between a high level and a low level.

Likewise, second signal input electrode 47b for inputting clock signal P2V to order transfer of charge, into pixel 43 is provided through an insulating film on the front surface side of the n⁻ layer 48c. This clock signal P2V switches its logical level in transfer of charge between a high level and a low level.

The clock signal P1V with the logical level at the low level is supplied to the first signal input electrode 47a during the image pickup operation. The clock signal P2V with the logical level at the low level is supplied to the second signal input electrode 47b during the image pickup operation.

The image sensor 100 with this CCD image pickup device 40 operates to perform image pickup in a disconnected state from the main body part 200. Two conditions are necessary for implementation of the image pickup in the disconnected state of the image sensor 100 from the main body part 200. The first condition is to supply the clock signal P1V with the logical level at the low level to the first signal input electrode 47a and supply the clock signal P2V with the logical level at the low level to the second signal input electrode 47b; the second condition is to supply the bias voltage ISV with the voltage value to be set in the integral time to the first bias voltage input electrode 46a, supply the bias voltage ISH with the image pickup voltage value to the second bias voltage input electrode 46b, and supply the bias voltage RD with the image pickup voltage value to the third bias voltage input electrode 46c.

The image sensor 100 according to the present embodiment is configured to satisfy the two conditions described above during the image pickup operation. The configuration will be described with reference to FIG. 5.

Figure 5:
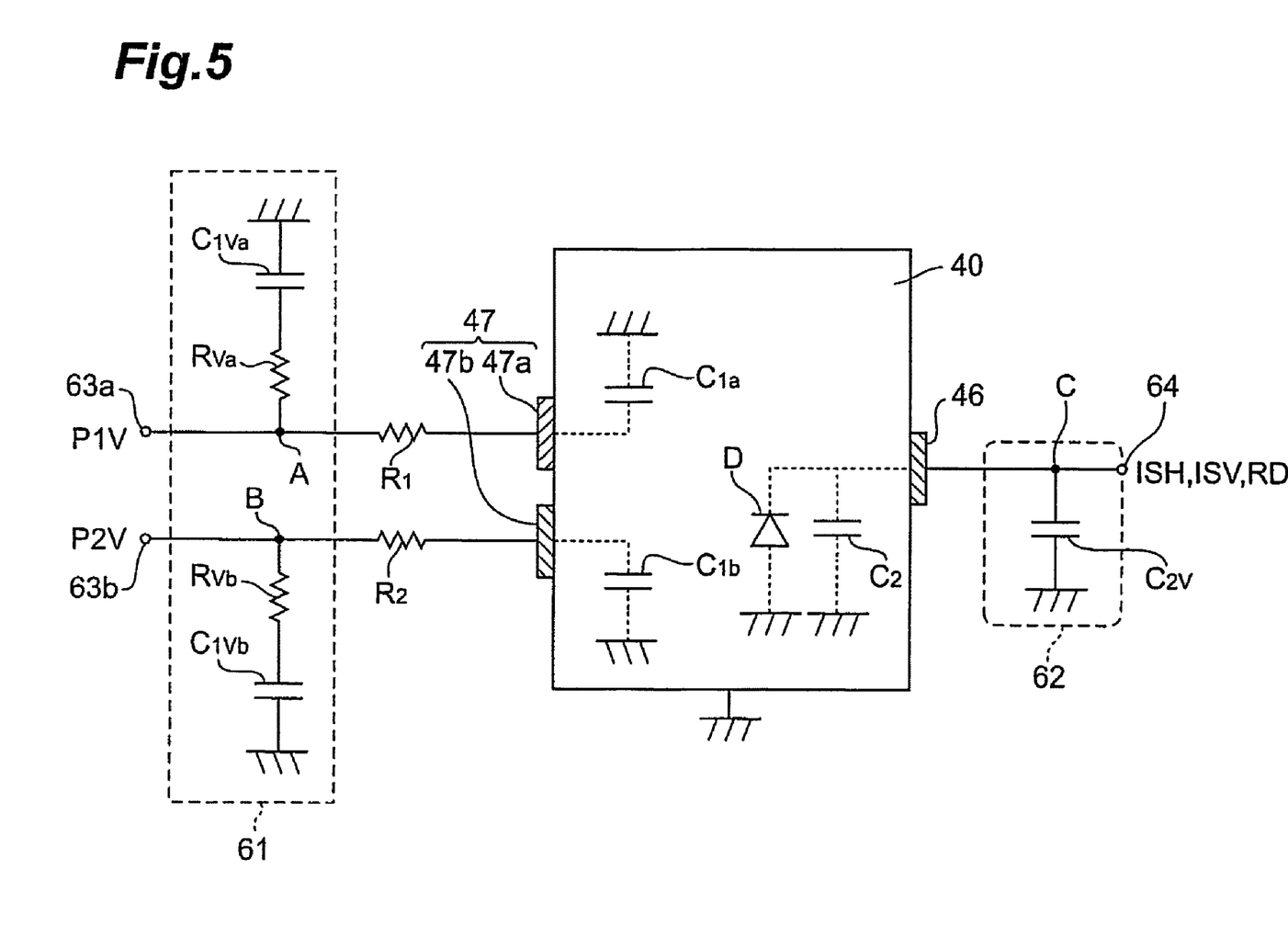
FIG. 5 is a diagram showing a configuration of CCD image pickup device 40, first signal input resistor $R_1$, second signal input resistor $R_2$, first voltage maintainer 61, and second voltage maintainer 62 in the image sensor 100 according to the embodiment.

FIG. 5 is a diagram showing the configuration of the CCD image pickup device 40, first signal input resistor $R_1$, second signal input resistor $R_2$, first voltage maintainer 61, and second voltage maintainer 62 in the image sensor 100 according to the present embodiment. FIG. 5 shows an equivalent circuit of the CCD image pickup device 40 as a view from the outside. FIG. 5 will be described using a bias voltage input electrode 46, instead of the first bias voltage input electrode 46a, second bias voltage input electrode 46b, and third bias voltage input electrode 46c shown in FIG. 4.

The CCD image pickup device 40 shown in FIG. 5 includes two first capacitors $C_{1a}$, $C_{1b}$ as an equivalent circuit of pixel 43, and includes a second capacitor $C_2$ and a diode D as an equivalent circuit of the region under the bias voltage input electrode 46.

The first capacitor $C_{1a}$ is connected to the first signal input electrode 47a at one end and is grounded at the other end. Similarly, the other first capacitor $C_{1b}$ is also connected to the second signal input electrode 47b at one end and is grounded at the other end.

The second capacitor $C_2$ is connected to the bias voltage input electrode 46 at one end and is grounded at the other end. The diode D is connected to the bias voltage input electrode 46 on the cathode side and is grounded on the anode side.

The first signal input resistor $R_1$ is connected to the first signal input electrode 47a at one end and to terminal 63a being an input terminal of the clock signal P1V, at the other end. The clock signal P1V supplied to the terminal 63a is fed through this first signal input resistor $R_1$ to the first signal input electrode 47a.

An ac-signal blocking resistor $R_{Va}$ included in the first voltage maintainer 61 is connected to a connection point A between the first signal input resistor $R_1$ and the terminal 63a at one end, and is connected to first voltage maintaining capacitor $C_{1Va}$ at the other end. Namely, the ac-signal blocking resistor $R_{Va}$ is connected between the first voltage maintaining capacitor $C_{1Va}$ and the terminal 63a.

The first voltage maintaining capacitor $C_{1Va}$ is connected to the ac-signal blocking resistor $R_{Va}$ at one end and is grounded at the other end. This first voltage maintaining capacitor $C_{1Va}$ is configured to maintain the first signal input electrode 47a at the voltage having the same voltage value as the voltage value of the clock signal P1V with the logical level at the low level, for implementing the image pickup in the disconnected state of the image sensor 100.

For maintaining the first signal input electrode 47a at the voltage, preferably, the first voltage maintaining capacitor $C_{1Va}$ has the capacitance 100 or more times greater than that of the first capacitor $C_{1a}$.

The second signal input resistor $R_2$ is connected to the second signal input electrode 47b at one end and to terminal 63b being an input terminal of the clock signal P2V, at the other end. The clock signal P2V supplied to the terminal 63b is fed through this first signal input resistor $R_2$ to the second signal input electrode 47b.

Another ac-signal blocking resistor $R_{Vb}$ is connected to a connection point B between the second signal input resistor $R_2$ and the terminal 63b at one end and is connected to another first voltage maintaining capacitor $C_{1Vb}$ at the other end. Namely, the other ac-signal blocking resistor $R_{Vb}$ is connected between the other first voltage maintaining capacitor $C_{1Vb}$ and the terminal 63b.

The other first voltage maintaining capacitor $C_{1Vb}$ is connected to the other ac-signal blocking resistor $R_{Vb}$ at one end and is grounded at the other end. The other first voltage maintaining capacitor $C_{1Vb}$ is configured to maintain the second signal input electrode 47b at the voltage having the same voltage value as the voltage value of the clock signal P2V with the logical level at the low level, for implementing the image pickup in the disconnected state of the image sensor 100.

For maintaining the second signal input electrode 47b at the voltage, preferably, the other first voltage maintaining capacitor $C_{1Vb}$ has the capacitance 100 or more times greater than that of the other first capacitor $C_{1b}$.

By providing the first voltage maintainer 61 including the two first voltage maintaining capacitors $C_{1Va}$, $C_{1Vb}$ in this way, it becomes feasible to maintain the first signal input electrode 47a at the voltage having the same voltage value as the voltage value of the clock signal P1V with the logical level at the low level and maintain the second signal input electrode 47b at the voltage having the same voltage value as the voltage value of the clock signal P2V with the logical level at the low level, even in the disconnected state of the image sensor 100 from the main body part 200.

The image sensor 100 according to the present embodiment has the two ac-signal blocking resistors $R_{Va}$, $R_{Vb}$. For keeping the clock signal P1V seldom entering the first voltage maintaining capacitor $C_{1Va}$, the ac-signal blocking resistor $R_{Va}$ has the resistance 100 or more times greater than that of the first signal input resistor $R_1$; for keeping the clock signal P2V seldom entering the other first voltage maintaining capacitor $C_{1Vb}$, the other ac-signal blocking resistor $R_{Vb}$ has the resistance 100 or more times greater than that of the second signal input resistor $R_2$.

When the first voltage maintainer 61 is provided with the two ac-signal blocking resistors $R_{Va}$, $R_{Vb}$ in addition to the two first voltage maintaining capacitors $C_{1Va}$, $C_{1Vb}$ in this way, the first signal input electrode 47a can be maintained at the voltage having the same voltage value as the voltage value of the clock signal P1V with the logical level at the low level and the clock signal P1V can be accurately supplied to the first signal input electrode 47a during the transfer of charge, even in the disconnected state of the image sensor 100 from the main body part 200. Similarly, the second signal input electrode 47b can be maintained at the voltage having the same voltage value as the voltage value of the clock signal P2V with the logical level at the low level, and the clock signal P2V can be accurately supplied to the second signal input electrode 47b during the transfer of charge.

The second voltage maintainer 62 has a second voltage maintaining capacitor $C_{2V}$. The second voltage maintaining capacitor $C_{2V}$ is connected to a connection point C between the bias voltage input electrode 46 and terminal 64 being an input terminal of the bias voltage ISH, ISV, RD at one end and is grounded at the other end.

This second voltage maintaining capacitor $C_{2V}$ is configured to maintain the bias voltage input electrode 46 at the voltage having the same voltage value as that of the bias voltage ISH, ISV, RD during the image pickup operation, for implementing use in the disconnected state of the image sensor 100. For maintaining the bias voltage input electrode 46 at the voltage, preferably, the second voltage maintaining capacitor $C_{2V}$ has the capacitance 100 or more greater than that of the second capacitor $C_2$.

By providing the second voltage maintainer 62 including the second voltage maintaining capacitor $C_{2V}$ in this way, it becomes feasible to maintain the bias voltage input electrode 46 at the voltage having the same voltage value as that of the bias voltage ISH, ISV, RD, even in the disconnected state of the image sensor 100 from the main body part 200.

As described above, the image sensor 100 of the present embodiment implements the image pickup in the isolated state of the image sensor 100, without need for the battery and the radio system, and the image sensor can be obtained in the inexpensive and simple configuration without need for the cable for connection to the main body part 200.

Since the image sensor 100 of the present embodiment has the two ac-signal blocking resistors $R_{Va}$, $R_{Vb}$, the clock signals P1V, P2V can be accurately supplied to the signal input electrodes 47 during the transfer of charge.

This image sensor 100 is connected to the main body part 200 after completion of the image pickup. The main body part 200 retrieves the electric signals according to amounts of charges generated in the respective pixels $43_{1,1}$–$43_{M,N}$ and generates image data based on the thus retrieved electric signals. The image data thus generated is printed as an image by a printer or displayed on a display device.

Figure 6:
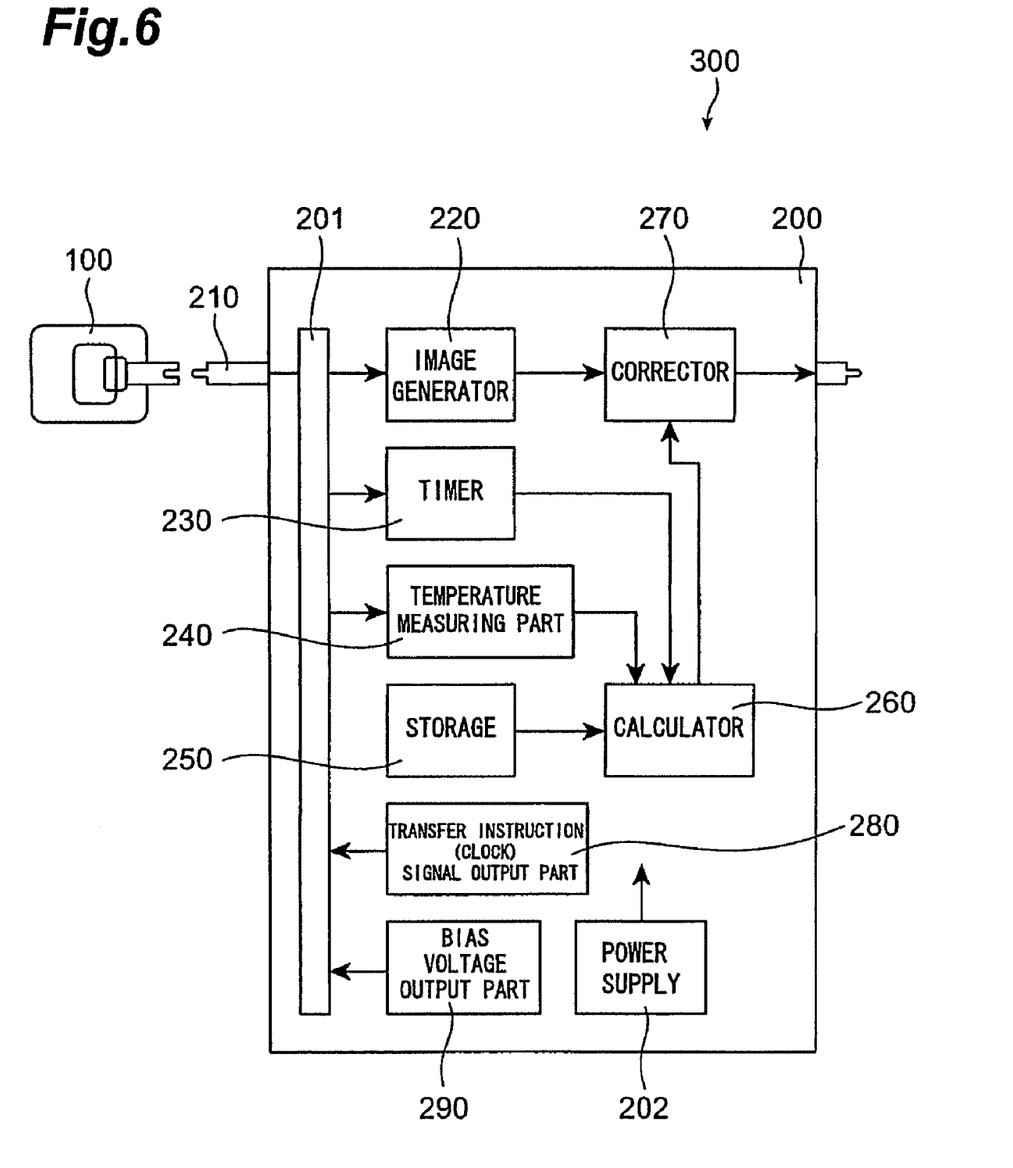
FIG. 6 is a block diagram showing a configuration of imaging system 300 according to an embodiment of the invention.

Next, an embodiment of the imaging system according to the present invention will be described. FIG. 6 is a block diagram showing the configuration of imaging system 300 according to the present embodiment. The imaging system 300 is comprised of image sensor 100 and main body part 200. The main body part 200 includes interface 201, power supply 202, connection part 210, image generator (image generating means) 220, timer (timer means) 230, temperature measuring part (temperature measuring means) 240, storage (storage means) 250, calculator (calculating means) 260, corrector (correcting means) 270, clock signal output part (clock signal outputting means) 280, and bias voltage output part (bias voltage outputting means) 290. The image sensor 100 is configured to be connected to the connection part 210 provided in the main body part 200.

The connection part 210 is an outgoing line such as a flexible cable, and is configured to be connected through a terminal provided at the distal end of the outgoing line, to the image sensor 100. The connection part 210 is connected to interface 201. This connection part 210 guides electric signals according to the charges generated in the respective pixels $43_{1,1}$–$43_{M,N}$, to the interface 201.

The connection part 210 also guides the clock signals P1V, P2V and the bias voltages ISV, ISH, RD from the interface 201 to the image sensor 100.

The interface 201 is connected to image generator 220, timer 230, temperature measuring part 240, clock signal output part 280, and bias voltage output part 290, and is configured to output the input signals from the image sensor 100 through the connection part 210, to the image generator 220, to the timer 230, and to the temperature measuring part 240 and to output the input signals from the clock signal output part 280 and the input bias voltage from the bias voltage output part 290, through the connection part 210 to the image sensor 100.

The image generator 220 retrieves the electric signals according to amounts of charges generated in the respective pixels $43_{1,1}$–$43_{M,N}$, through the connection part 210 and interface 201. The image generator 220 generates image data based on the electric signals. The image generator 220 is connected to the corrector 270 and outputs the image data thus generated, to the corrector 270.

The timer 230 acquires a value of the integral time being a period of time in which the supply of the clock signals P1V, P2V to the signal input electrodes 47 is suspended. This integral time is measured using an integral start switch (not shown) and an integral end switch (not shown) provided in the main body part 200, and an integral operation is started with a depression of the integral start switch and terminated with a depression of the integral end switch.

Figure 7:
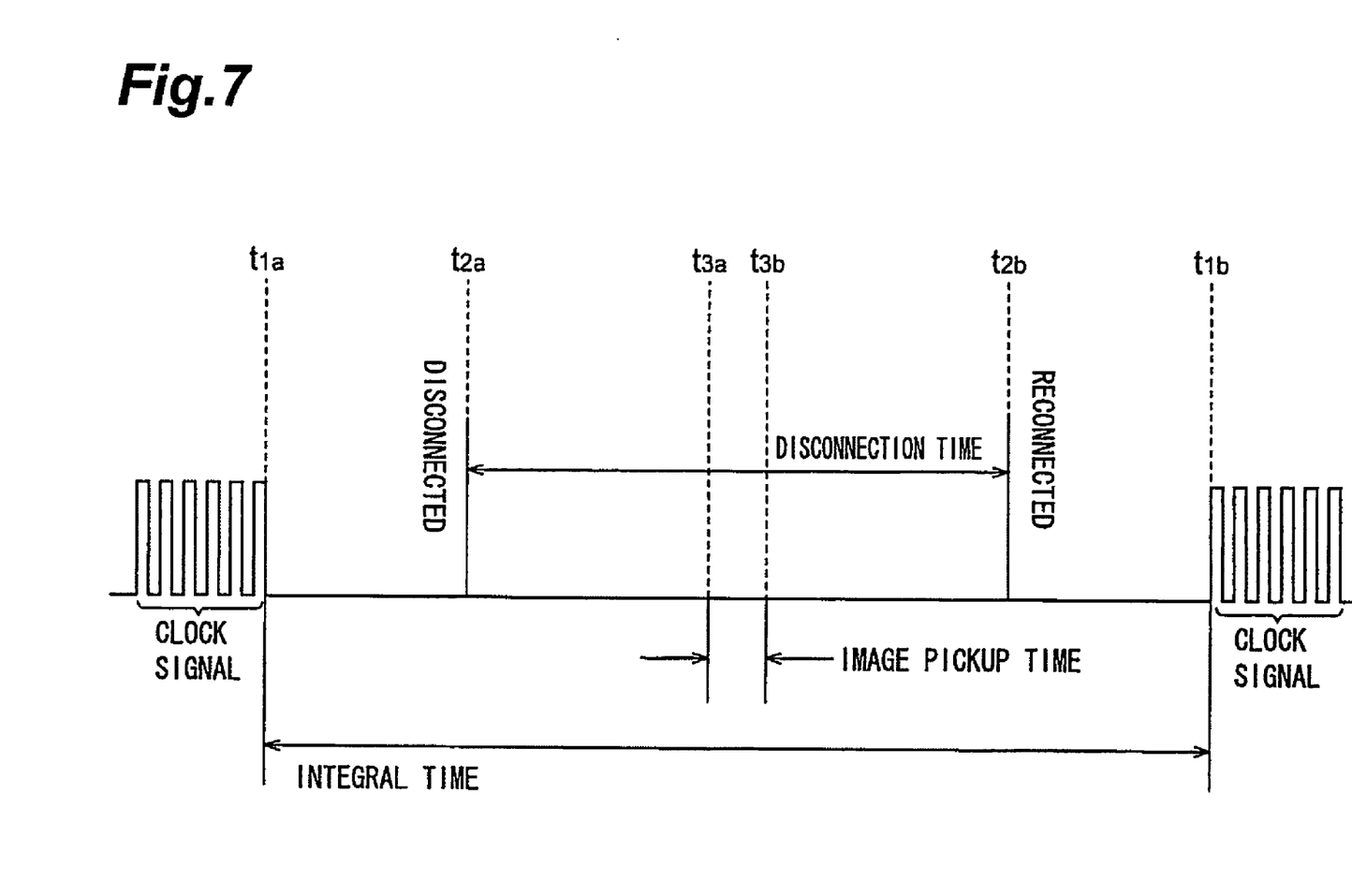
FIG. 7 is a timing chart to illustrate measurement of integral time in main body part 200 of the imaging system 300 according to the embodiment.

Here the integral time will be further described with reference to FIG. 7. FIG. 7 is a timing chart to illustrate the measurement of the integral time in the main body part 200 of the imaging system 300 according to the present embodiment. It is assumed herein that the main body part 200 is provided with the integral start switch and the integral end switch.

First, a user or the like depresses the integral start switch at time $t_{1a}$. When this switch is depressed, the clock signals P1V, P2V stop entering the signal input electrodes 47. At this time, the two first voltage maintaining capacitors $C_{1Va}$, $C_{1Vb}$ maintain the voltage of the signal input electrodes 47 at the voltage having the same voltage value as that of the clock signals P1V, P2V with the logical level at the L (low) level.

Thereafter, the image sensor 100 is disconnected from the connection part 210 of the main body part 200 at time $t_{2a}$. At time $t_{3a}$ thereafter the image sensor 100 starts being exposed to X-rays.

Thereafter, the injection of X-rays into the image sensor 100 is terminated at time $t_{3b}$. Then the image sensor 100 is connected to the connection part 210 at time $t_{2b}$. Thereafter, the user or the like depresses the integral end switch at time $t_{1b}$. When the integral end switch is depressed, the clock signals P1V, P2V start entering the signal input electrodes 47.

The period from time $t_{1a}$ to time $t_{1b}$ is the integral time. This integral time is different from a disconnection time being a period from time $t_{2a}$ to time $t_{2b}$ and also different from an image pickup time being a period from time $t_{3a}$ to time $t_{3b}$. The period from time $t_{1a}$ to time $t_{1b}$ is also a period of time in which charges generated by dark current are stored. The timer 230 measures this integral time.

If the main body part 200 is not provided with the integral start switch and the integral end switch, the timer 230 can be arranged to measure the time from the disconnection of the image sensor 100 from the connection part 210 to the connection to the connection part 210, as the integral time. When this method is employed, the period from time $t_{2a}$ to time $t_{2b}$ shown in FIG. 7 coincides with the period from time $t_{1a}$ to time $t_{1b}$.

The integral time measured in this way is used as data of the value of integral time. The timer 230 is connected to the calculator 260 and outputs the data of the value of integral time thus measured, to the calculator 260.

The temperature measuring part 240 measures the temperature of the image sensor 100 during the period from the disconnection of the image sensor 100 from the connection part 210 to the connection to the connection part 210. Namely, it measures the temperature of the image sensor 100 for the disconnection time. For example, the temperature measuring part 240 starts the measurement of temperature by detecting a disconnection of image sensor 100 and ends the measurement of temperature by detecting a connection of image sensor 100, while acquiring connection information indicating whether the image sensor 100 is connected to the connection part 210, through the interface 201. The temperature measured is used as data of the value of temperature. In this case, the temperature measuring part 240 measures the ambient temperature of the main body part 200 as the temperature of the image sensor 100. The temperature measuring part 240 is connected to the calculator 260 and outputs the data of value of temperature thus measured, to the calculator 260.

The storage 250 stores dark current image data according to amounts of charges generated in the respective pixels $43_{1,1}$–$43_{M,N}$ by dark current. For example, under a situation in which no light is incident into the image sensor 100, image data according to amounts of charges generated by dark current flowing at that time is stored in the storage. The storage 250 is connected to the calculator 260 and outputs the dark current image data stored, to the calculator 260.

The calculator 260 stores a function with variables one being the temperature of the image sensor 100 and the other being the time of suspension of supply of the clock signals P1V, P2V to the signal input electrodes 47. The calculator 260 calculates corrected image data on the basis of this function and the dark current image data stored in the storage 250. At this time, the calculator 260 retrieves the data of value of integral time from the timer 230 and the data of value of temperature from the temperature measuring part 240 and calculates the corrected image data by substituting the value of integral time measured by the timer 230 and the value of temperature measured by the temperature measuring part 240, into the stored function. The calculator 260 is connected to the corrector 270 and outputs the corrected image data thus calculated, to the corrector 270.

The corrector 270 corrects the image data generated by the image generator 220, on the basis of the corrected image data calculated by the calculator 260. After the correction, the corrector 270 outputs the thus corrected image data to a device such as a printer or a display.

The clock signal output part 280 outputs the clock signals P1V, P2V through interface 201 and connection part 210 to the signal input electrodes 47 of the image sensor 100. The bias voltage output part 290 outputs the bias voltages ISH, ISV, RD through interface 201 and connection part 210 to the bias voltage input electrodes 46 of the image sensor 100. The clock signals P1V, P2V from the clock signal output part 280 and the bias voltages ISH, ISV, RD from the bias voltage output part 290 are supplied to the CCD image pickup device 40 of the image sensor 100, whereby the image sensor 100 becomes able to transfer the charges generated in the respective pixels $43_{1,1}$–$43_{M,N}$ and output the electric signals according to the charges generated in the respective pixels $43_{1,1}$–$43_{M,N}$. The power supply 202 supplies power to each of the components of the main body part 200 and to the image sensor 100.

Next, the operation of the main body part 200 will be described. The description will be given herein on the assumption that the main body part 200 is provided with the integral start switch and the integral end switch.

First, the user depresses the integral start switch provided in the main body part 200, whereupon the timer 230 starts measuring the integral time. Thereafter, the image sensor 100 before an image pickup operation is disconnected from the connection part 210 of the main body part 200. At this time, the temperature measuring part 240 starts measuring the temperature. Thereafter, the image sensor 100 after completion of the image pickup is connected to the connection part 210 of the main body part 200. At this time, the temperature measuring part 240 ends the measurement of temperature.

Then the user depresses the integral end switch provided in the main body part 200, whereupon the timer 200 terminates the measurement of integral time. At this time, the clock signal output part 280 outputs the clock signals P1V, P2V to the signal input electrodes 47 of the image sensor 100 and the bias voltage output part 290 outputs the bias voltages ISH, ISV, RD to the bias voltage input electrodes 46 of the image sensor 100. This causes the transfer of charges generated in the respective pixels $43_{1,1}$–$43_{M,N}$ and the output of the electric signals according to the charges generated in the respective pixels $43_{1,1}$–$43_{M,N}$.

The output electric signals are fed through the interface 201 to the image generator 220. The image generator 220 generates the image data on the basis of the input electric signals. The image data generated by the image generator 220 is fed to the corrector 270.

During this period, the data of value of integral time measured by the timer 230 is fed to the calculator 260, the data of value of temperature measured by the temperature measuring part 240 to the calculator 260, and the dark current image data stored in the storage 250, to the calculator 260.

The calculator 260 generates the corrected image data from the data of value of integral time, the data of value of temperature, the dark current image data, and the stored function and outputs the corrected image data to the corrector 270.

The image data outputted from the image generator 220 is corrected based on this corrected image data, by the corrector 270. Thereafter, the image data after the correction is outputted to the display, the printer, or the like.

As described above, the imaging system 300 according to the present embodiment is able to generate the image data by use of the aforementioned image sensor 100. The imaging system 300 of the present embodiment is also able to make the correction according to the amounts of charges generated in the respective pixels $43_{1,1}$–$43_{M,N}$ by dark current. The imaging system 300 of the present embodiment is also able to calculate the corrected image data on the basis of the measured integral time and make the correction for the image data on the basis of the corrected image data. The imaging system 300 of the present embodiment is also able to calculate the corrected image data on the basis of the measured temperature and make the correction for the image data on the basis of the corrected image data.

Although in the present embodiment the calculator 260 retrieves the dark current data, the data of value of integral time, and the data of value of temperature and calculates the corrected image data, the invention does not have to be limited to this configuration and the system may be arranged so that the calculator 260 calculates the corrected data on the basis of the dark current image data and the data of value of integral time, on the basis of the dark current data and the data of value of temperature, or on the basis of only the dark current data.

In the present embodiment the temperature measuring part 240 measured the ambient temperature of the main body part 200, but, without having to be limited to this, the system may also be configured to be provided with a means for measuring the temperature, in the image sensor 100 and to output the data of measured value to the main body part 200.

The present embodiment employed the two-phase charge transfer method, but the charge transfer method does not have to be limited to this and may be a single-phase, or three or more phase transfer method. In these cases, voltage maintaining capacitors have to be prepared by the number according to each transfer method. Namely, in the case of the three-phase transfer method, three voltage maintaining capacitors are needed; in the case of the four-phase transfer method, four voltage maintaining capacitors are needed; in the case of the single-phase transfer method, one voltage maintaining capacitor is needed.

INDUSTRIAL APPLICABILITY

The image sensor and the imaging system using the image sensor according to the present invention are applicable, for example, to X-ray inspection of mouth cavity.

The invention claimed is:

1. An image sensor having an image pickup part including an array of pixels to generate their respective charges in response to incidence of light, a readout part for outputting electric signals according to the charges generated in the respective pixels, a signal input electrode for inputting a clock signal to order transfer of the charge, into each of the pixels, and a bias voltage input electrode for inputting a bias voltage supplied to the image pickup part and to the readout part, said image sensor comprising:
first voltage maintaining means connected to the signal input electrode and comprising a first voltage maintaining capacitor for maintaining a voltage of the signal input electrode, a terminal through which the clock signal is inputted and which is electrically connected to the signal input electrode, and an ac-signal blocking resistor connected between the first voltage maintaining capacitor and the terminal; and
second voltage maintaining means connected to the bias voltage input electrode and comprising a second voltage maintaining capacitor for maintaining a voltage of the bias voltage input electrode.

2. An imaging system comprising the image sensor as set forth in claim 1, and a main body part,
wherein said main body part comprises:
a connector part enabling connection and disconnection of the image sensor;
clock signal outputting means for outputting the clock signal through the connector part to the signal input electrode of the image sensor;
bias voltage outputting means for outputting the bias voltage through the connector part to the bias voltage input electrode of the image sensor; and
image generating means for retrieving the electric signals according to amounts of the charges generated in the respective pixels, outputted from the image sensor, through the connector part and generating image data on the basis of the electric signals.

3. The imaging system according to claim 2, further comprising:

storage means for storing image data of dark current according to amounts of charges generated in the respective pixels by dark current;

calculating means for calculating corrected image data on the basis of the dark current image data stored in the storage means; and correcting means for correcting the image data generated by the image generating means, on the basis of the corrected image data calculated by the calculating means.

4. The imaging system according to claim 3, further comprising:

timer means for acquiring a value of integral time being a period of time in which input of the clock signal to the signal input electrode is suspended, wherein the calculating means calculates the corrected image data on the basis of the value of integral time obtained by the timer means.

5. The imaging system according to claim 3, further comprising:

temperature measuring means for measuring temperature of the image sensor during a period between a disconnection of the image sensor from the connector part and a connection of the image sensor to the connector part to acquire a value of the temperature, wherein the calculating means calculates the corrected image data on the basis of the value of the temperature acquired by the temperature measuring means.

6. An image sensor capable of picking up an image in a state in which the image sensor is disconnected from a main body part provided with a voltage supply part, said image sensor comprising:

an image pickup part comprising an array of pixels each comprised of a photoelectric conversion part to generate a charge in response to incidence of light and a signal input electrode for inputting a clock signal to order transfer of the charge;

a readout part for outputting electric signals according to the charges generated in the respective pixels;

a bias voltage input electrode for inputting a bias voltage supplied to the photoelectric conversion part and to the readout part;

a clock signal input terminal for receiving supply of the clock signal from the main body part when the image sensor is connected to the main body part;

first voltage maintaining means connected to the signal input electrode in parallel with the clock signal input terminal and comprising a first voltage maintaining capacitor for maintaining a voltage of the signal input electrode;

a bias voltage input terminal for receiving supply of the bias voltage from the main body part when the image sensor is connected to the main body part; and second voltage maintaining means connected to the bias voltage input electrode in parallel with the bias voltage input terminal and comprising a second voltage maintaining capacitor for maintaining a voltage of the bias voltage input electrode.

7. The image sensor according to claim 6, wherein said first voltage maintaining means comprises an ac-signal blocking resistor connected in series to the first voltage maintaining capacitor.

* * * * *